United States Patent
von Haken Spence et al.

(10) Patent No.: US 6,355,744 B1
(45) Date of Patent: *Mar. 12, 2002

(54) CYCLOPENTADIENYL/PHOSPHINIMINE CATALYST WITH ONE AND ONLY ONE ACTIVATABLE LIGAND

(75) Inventors: Rupert Edward von Haken Spence, Calgary; Douglas W. Stephan, LaSalle; Stephen John Brown, Calgary; Dusan Jeremic, Calgary; Qinyan Wang, Calgary, all of (CA)

(73) Assignee: Nova Chemicals (International) S.A. (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/656,158

(22) Filed: Sep. 6, 2000

Related U.S. Application Data

(63) Continuation of application No. 09/328,818, filed on Jun. 9, 1999, now abandoned.

(30) Foreign Application Priority Data

Jul. 21, 1998 (CA) .............................................. 2243726

(51) Int. Cl.$^7$ .............................. C08F 4/44; B01J 31/00
(52) U.S. Cl. ........................ 526/127; 526/160; 526/161; 526/352; 526/943; 502/152; 502/155
(58) Field of Search ................................ 526/127, 160, 526/161, 352, 945; 502/155, 152

(56) References Cited

U.S. PATENT DOCUMENTS

| | | | |
|---|---|---|---|
| 4,542,199 A | 9/1985 | Kaminsky et al. | |
| 4,543,399 A | 9/1985 | Jenkins, III et al. | |
| 4,752,597 A | 6/1988 | Turner | |
| 4,808,561 A | 2/1989 | Welborn, Jr. | |
| 5,198,401 A | 3/1993 | Turner et al. | |
| 5,324,800 A | 6/1994 | Welborn, Jr. et al. | |
| 5,352,749 A | 10/1994 | De Chellis et al. | |
| 5,648,310 A | 7/1997 | Wasserman et al. | |
| 5,672,669 A | 9/1997 | Wasserman et al. | |
| 5,674,795 A | 10/1997 | Wasserman et al. | |
| 5,965,677 A | * 10/1999 | Stephan et al. | ............. 526/129 |

* cited by examiner

Primary Examiner—David W. Wu
Assistant Examiner—R. Harlan
(74) Attorney, Agent, or Firm—Kenneth H. Johnson

(57) ABSTRACT

Organometallic complexes of titanium or zirconium having only three ligands (namely a cyclopentadienyl ligand, a phosphinimine ligand and an activatable ligand) are catalyst components for olefin polymerization. Preferred polymerization systems are prepared by combining the organometallic complexes with an ionic activator and/or an alumoxane. Preferred catalyst components contain titanium (III) and are used in ethylene polymerization.

4 Claims, No Drawings

CYCLOPENTADIENYL/PHOSPHINIMINE CATALYST WITH ONE AND ONLY ONE ACTIVATABLE LIGAND

This is a continuation, of application Ser. No. 09/328,818, filed Jun. 9, 1999 now abandoned.

FIELD OF THE INVENTION

This invention relates to an olefin polymerization catalyst component which is an organometallic complex having three ligands, namely a cyclopentadienyl ligand, a phosphinimine ligand and only one activatable ligand.

BACKGROUND OF THE INVENTION

Certain "metallocenes" (especially bis-cyclopentadienyl complexes of group 4 metals) are highly productive catalysts for olefin polymerization when used in combination with an appropriate activator (see, for example, U.S. Pat. No. 4,542,199 (Sinn et al) and U.S. Pat. No. 5,198,401 (Hlatky and Turner).

Olefin polymerization catalysts which contain a group 4 metal and one cyclopentadienyl ligand, one phosphinimine ligand and two monoanionic activatable ligands are disclosed in a commonly assigned patent application (Stephan et al). Thus, the catalysts of Stephan et al are group 4 metals in the 4+ oxidation state.

We have now discovered a new family of olefin polymerization catalysts which contain a group 4 metal, a cyclopentadienyl ligand or phosphinimine ligand and only one activatable ligand. A preferred family of these catalysts contains Ti(III) and offers an excellent kinetic profile when used in olefin polymerization.

SUMMARY OF THE INVENTION

The present invention provides a catalyst component for olefin polymerization which is an organometallic complex defined by the formula:

wherein Cp is a cyclopentadienyl-type ligand; L is an activatable ligand; M is a metal selected from Ti and Zr; and PI is a phosphinimine ligand defined by the formula:

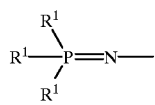

wherein each $R^1$ is independently selected from the group consisting of a hydrogen atom, a halogen atom, $C_{1-20}$ hydrocarbyl radicals which are unsubstituted by or further substituted by a halogen atom, a $C_{1-8}$ alkoxy radical, an amido radical, a $C_{6-10}$ aryl or aryloxy radical, a silyl radical of the formula:

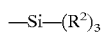

wherein each $R^2$ is independently selected from the group consisting of hydrogen, a $C_{1-8}$ alkyl or alkoxy radical, $C_{6-10}$ aryl or aryloxy radicals, and a germanyl radical of the formula:

wherein $R^2$ is as defined above.

DETAILED DESCRIPTION

1. Description of Catalyst Component 1.1 Metals

The catalyst component of this invention is a group 4 metal selected from titanium and zirconium.

1.2 Phosphinimine Ligand

The catalyst component of this invention must contain a phosphinimine ligand which is covalently bonded to the metal. This ligand is defined by the formula:

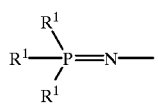

wherein each $R^1$ is independently selected from the group consisting of a hydrogen atom, a halogen atom, $C_{1-20}$ hydrocarbyl radicals which are unsubstituted by or further substituted by a halogen atom, a $C_{1-8}$ alkoxy radical, a $C_{6-10}$ aryl or aryloxy radical, an amido radical, a silyl radical of the formula:

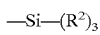

wherein each $R^2$ is independently selected from the group consisting of hydrogen, a $C_{1-8}$ alkyl or alkoxy radical, $C_{6-10}$ aryl or aryloxy radicals, and a germanyl radical of the formula:

wherein $R^2$ is as defined above.

The preferred phosphinimines are those in which each $R^1$ is a hydrocarbyl radical. A particularly preferred phosphinimine is tri-(tertiary butyl) phosphinimine (i.e. where each $R^1$ is a tertiary butyl group).

1.3 Cyclopentadienyl-Type Ligand

The term cyclopentadienyl-type ligand (or "Cp ligand") refers to a ligand which is cyclic and forms a delocalized pi-bond with the group 4 transition metal. An exemplary (i.e. illustrative but non-limiting) list of "Cp ligands" includes substituted (or unsubstituted) cyclopentadienyl ligands, substituted (or unsubstituted) indenyl ligands, and substituted (or unsubstituted) fluorenyl ligands.

The use of "substituents" on such cyclic ligands is well known and is described, for example, in U.S. Pat. No. 5,324,800 (Welborn). An exemplary list of substituents for such Cp ligands includes $C_{1-20}$ hydrocarbyl groups; substituted $C_{1-20}$ hydrocarbyl groups wherein one or more hydrogen atoms is replaced by a halogen; an amido group, a phosphido group, or an alkoxy group. The substituent may form a bridge with the phosphinimine ligand.

For reasons of cost and simplicity, it is especially preferred that the Cp ligand is a cyclopentadienyl or indenyl ligand.

1.4 Activatable Ligand

The term "activatable ligand" refers to a ligand which may be activated by a cocatalyst (also known as an "activator" to facilitate olefin polymerization. Exemplary activatable ligands are independently selected from the group consisting of a hydrogen atom, a halogen atom, a $C_{1-10}$ hydrocarbyl radical, a $C_{1-10}$ alkoxy radical, a $C_{5-10}$ aryl oxide radical; each of which said hydrocarbyl, alkoxy, and aryl oxide radicals may be unsubstituted by or further substituted by a halogen atom, a $C_{1-8}$ alkyl radical, a $C_{1-8}$ alkoxy radical, a $C_{6-10}$ aryl or aryl oxy radical, an amido radical which is unsubstituted or substituted by up to two $C_{1-8}$ alkyl radicals; a phosphido radical which is unsubstituted or substituted by up to two $C_{1-8}$ alkyl radicals.

2. Description of Activators (or "Cocatalysts")

The catalyst components described in part 1 above are used in combination with an "activator" (which may also be referred to by a person skilled in the art as a "cocatalyst") to form an active catalyst system for olefin polymerization. Simple aluminum alkyls and alkoxides may provide comparatively weak cocatalytic activity under certain mild polymerization conditions. However, the preferred activators are alumoxanes and so-called ionic activators, as described below.

2.1 Alumoxanes

The alumoxane activator may be of the formula:

$(R^4)_2AlO(R^4AlO)_mAl(R^4)_2$ wherein each $R^4$ is independently selected from the group consisting of $C_{1-20}$ hydrocarbyl radicals and m is from 0 to 50, preferably $R^4$ is a $C_{1-4}$ alkyl radical and m is from 5 to 30. Methylalumoxane (or "MAO") is the preferred alumoxane.

Alumoxanes are well known as activators for metallocene-type catalysts.

Activation with alumoxane generally requires a molar ratio of aluminum in the activator to (group 4) metal in the catalyst from 20:1 to 1000:1. Preferred ratios are from 50:1 to 250:1.

2.2 Ionic Activators

Ionic activators are also well known for metallocene catalysts. See, for example, U.S. Pat. No. 5,198,401 (Hlatky and Turner). These compounds may be selected from the group consisting of:

(i) compounds of the formula $[R^5]^+[B(R^7)_4]^-$ wherein B is a boron atom, $R^5$ is a cyclic $C_{5-7}$ aromatic cation or a triphenyl methyl cation and each $R^7$ is independently selected from the group consisting of phenyl radicals which are unsubstituted or substituted with from 3 to 5 substituents selected from the group consisting of a fluorine atom, a $C_{1-4}$ alkyl or alkoxy radical which is unsubstituted or substituted by a fluorine atom; and a silyl radical of the formula —Si—$(R^9)_3$; wherein each $R^9$ is independently selected from the group consisting of a hydrogen atom and a $C_{1-4}$ alkyl radical; and (ii) compounds of the formula $[(R^8)_tZH]^+[B(R^7)_4]^-$ wherein B is a boron atom, H is a hydrogen atom, Z is a nitrogen atom or phosphorus atom, t is 2 or 3 and $R^8$ is selected from the group consisting of $C_{1-8}$ alkyl radicals, a phenyl radical which is unsubstituted or substituted by up to three $C_{1-4}$ alkyl radicals, or one $R^8$ taken together with the nitrogen atom may form an anilinium radical and $R^7$ is as defined above; and (iii) compounds of the formula $B(R^7)_3$ wherein $R^7$ is as defined above.

In the above compounds preferably $R^7$ is a pentafluorophenyl radical, and $R^5$ is a triphenylmethyl cation, Z is a nitrogen atom and $R^8$ is a $C_{1-4}$ alkyl radical or $R^8$ taken together with the nitrogen atom forms an anilinium radical which is substituted by two $C_{1-4}$ alkyl radicals.

The "ionic activator" may abstract the activatable ligand so as to ionize the catalyst center into a cation but not to covalently bond with the catalyst and to provide sufficient distance between the catalyst and the ionizing activator to permit a polymerizable olefin to enter the resulting active site.

Examples of ionic activators include:
triethylammonium tetra(phenyl)boron,
tripropylammonium tetra(phenyl)boron,
tri(n-butyl)ammonium tetra(phenyl)boron,
trimethylammonium tetra(p-tolyl)boron,
trimethylammonium tetra(o-tolyl)boron,
tributylammonium tetra(pentafluorophenyl)boron,
tripropylammonium tetra(o,p-dimethylphenyl)boron,
tributylammonium tetra(m,m-dimethylphenyl)boron,
tributylammonium tetra(p-trifluoromethylphenyl)boron,
tributylammonium tetra(pentafluorophenyl)boron,
tri(n-butyl)ammonium tetra(o-tolyl) boron
N,N-dimethylanilinium tetra(phenyl)boron,
N,N-diethylanilinium tetra(phenyl)boron,
N,N-diethylanilinium tetra(phenyl)n-butylboron,
N,N-2,4,6-pentamethylanilinium tetra(phenyl)boron
di-(isopropyl)ammonium tetra(pentafluorophenyl)boron,
dicyclohexylammonium tetra(phenyl)boron
triphenylphosphonium tetra(phenyl)boron,
tri(methylphenyl)phosphonium tetra(phenyl)boron,
tri(dimethylphenyl)phosphonium tetra(phenyl)boron,
tropillium tetrakispentafluorophenyl borate,
triphenylmethylium tetrakispentafluorophenyl borate,
benzene (diazonium) tetrakispentafluorophenyl borate,
tropillium phenyltrispentafluorophenyl borate,
triphenylmethylium phenyltrispentafluorophenyl borate,
benzene (diazonium) phenyltrispentafluorophenyl borate,
tropillium tetrakis (2,3,5,6-tetrafluorophenyl) borate,
triphenylmethylium tetrakis (2,3,5,6-tetrafluorophenyl) borate,
benzene (diazonium) tetrakis (3,4,5-trifluorophenyl) borate,
tropillium tetrakis (3,4,5-trifluorophenyl) borate,
benzene (diazonium) tetrakis (3,4,5-trifluorophenyl) borate,
tropillium tetrakis (1,2,2-trifluoroethenyl) borate,
triphenylmethylium tetrakis (1,2,2-trifluoroethenyl) borate,
benzene (diazonium) tetrakis (1,2,2-trifluoroethenyl) borate,
tropillium tetrakis (2,3,4,5-tetrafluorophenyl) borate,
triphenylmethylium tetrakis (2,3,4,5-tetrafluorophenyl) borate, and
benzene (diazonium) tetrakis (2,3,4,5-tetrafluorophenyl) borate.

Readily commercially available ionic activators include: N,N-dimethylaniliniumtetrakispentafluorophenyl borate; triphenylmethylium tetrakispentafluorophenyl borate; and trispentafluorophenyl borane.

3. Homogeneous or Heterogeneous Catalyst

The catalyst system of this invention may be used in a homogeneous form in solution polymerization (where the term "homogeneous" means that the catalyst and cocatalyst/activator are soluble in, or miscible with, the polymerization solvent). However, when the catalyst is employed in a slurry or gas phase polymerization, it is highly preferred to use the catalyst in a heterogeneous or "supported form". It is also highly preferred that the catalyst does not cause reactor fouling. The art of preparing heterogeneous catalysts which do not lead to reactor fouling is not adequately understood, though it is generally accepted that the catalytic material should be very well anchored to the support so as to reduce the incidence of fouling resulting from the deposition of catalyst or cocatalyst which has dissociated from the support.

In general, heterogeneous catalysts may be grouped into three main categories:

3.1. Unsupported Alumoxane/Catalyst Mixtures

These catalysts may be easily prepared by evaporating the solvent or diluent from a liquid mixture of an alumoxane and the catalyst component. The resulting product is a solid at room temperature due to the comparatively high molecular weight of the alumoxane. There are two disadvantages to this approach, namely cost (i.e. alumoxanes are comparatively expensive—and the alumoxane is used as an expensive "support" material) and "reaction continuity/fouling" (i.e. the alumoxane may partially melt under polymerization conditions, leading to reactor instability/fouling). U.S. Pat. No. 4,752,597 (Turner, to Exxon) illustrates this approach for the preparation of a heterogeneous catalyst.

3.2. Metal Oxide Supported Catalysts

These catalysts are prepared by depositing the catalyst component and a cocatalyst on a very porous metal oxide support. The catalyst and cocatalyst are substantially contained within the pore structure of the metal oxide particle. This means that a comparatively large metal oxide particle is used (typically particle size of from 40 to 80 microns). The preparation of this type of supported catalyst is described in U.S. Pat. No. 4,808,561 (Welborn, to Exxon).

3.3. Filled/Spray Dried Catalysts

This method of catalyst preparation is also well known. For example, U.S. Pat. Nos. 5,648,310; 5,674,795 and 5,672,669 (all to Union Carbide) teach the preparation of a heterogeneous catalyst by spray drying a mixture which contains a metallocene catalyst, an alumoxane cocatalyst and a "filler" which is characterized by having a very small particle size (less than one micron) and by being unreactive with the catalyst and cocatalyst. The examples illustrate the use of very fine particle size "fumed" silica which has been treated to reduce the concentration of surface hydroxyls. The resulting catalysts exhibit good productivity. Moreover, they offer the potential to provide a catalyst which is not prone to "hot spots" (as the catalyst may be evenly distributed, at low concentration, throughout the heterogeneous matrix). However, these catalysts suffer from the potential disadvantage of being very friable because they are prepared with a fine, "inert" filler material which does not react with/anchor to the catalyst or cocatalyst.

Friable catalyst particles lead to the formation of "fines" in the polyethylene product, and may also aggravate reactor fouling problems.

An alternative approach is the preparation of spray dried catalysts using a hydrotalcite as a "reactive" filler (as opposed to the unreactive filler described in the above-mentioned U.S. Patent to Union Carbide). This method of catalyst preparation is described in more detail in a commonly assigned patent application. Either approach is suitable for use with the catalysts of this invention.

4. Polymerization Processes

The catalysts of this invention are suitable for use in any conventional olefin polymerization process, such as the so-called "gas phase", "slurry", "high pressure" or "solution" polymerization processes.

The use of a heterogeneous catalyst is preferred for gas phase and slurry processes whereas a homogeneous catalyst is preferred for the solution process.

The polymerization process according to this invention uses ethylene and may include other monomers which are copolymerizable therewith such as other alpha olefins (having from three to ten carbon atoms, preferably butene, hexene or octene) and, under certain conditions, dienes such as hexadiene isomers, vinyl aromatic monomers such as styrene or cyclic olefin monomers such as norbornene.

The present invention may also be used to prepare elastomeric co- and terpolymers of ethylene, propylene and optionally one or more diene monomers. Generally, such elastomeric polymers will contain about 50 to abut 75 weight % ethylene, preferably about 50 to 60 weight % ethylene and correspondingly from 50 to 25% of propylene. A portion of the monomers, typically the propylene monomer, may be replaced by a conjugated diolefin. The diolefin may be present in amounts up to 10 weight % of the polymer although typically is present in amounts from about 3 to 5 weight %. The resulting polymer may have a composition comprising from 40 to 75 weight % of ethylene, from 50 to 15 weight % of propylene and up to 10 weight % of a diene monomer to provide 100 weight % of the polymer. Preferred but not limiting examples of the dienes are dicyclopentadiene, 1,4-hexadiene, 5-methylene-2-norbornene, 5-ethylidene-2-norbornene and 5-vinyl-2-norbornene. Particularly preferred dienes are 5-ethylidene-2-norbornene and 1,4-hexadiene.

The polyethylene polymers which may be prepared in accordance with the present invention typically comprise not less than 60, preferably not less than 70 weight % of ethylene and the balance one or more $C_{4-10}$ alpha olefins, preferably selected from the group consisting of 1-butene, 1-hexene and 1-octene. The polyethylene prepared in accordance with the present invention may be linear low density polyethylene having density from about 0.910 to 0.935 g/cc. The present invention might also be useful to prepare polyethylene having a density below 0.910 g/cc—the so-called very low and ultra low density polyethylenes.

The most preferred polymerization process of this invention encompasses the use of the novel catalysts (together with a cocatalyst) in a medium pressure solution process. As used herein, the term "medium pressure solution process" refers to a polymerization carried out in a solvent for the polymer at an operating temperature from 100 to 320° C. (especially from 120 to 220° C.) and a total pressure of from 3 to 35 mega Pascals. Hydrogen may be used in this process to control (reduce) molecular weight. Optimal catalyst and cocatalyst concentrations are affected by such variables as temperature and monomer concentration but may be quickly optimized by non-inventive tests.

Further details concerning the medium pressure polymerization process are well known to those skilled in the art and widely described in the open and patent literature.

The catalyst of this invention may also be used in a slurry polymerization process or a gas phase polymerization process.

The typical slurry polymerization process uses total reactor pressures of up to about 50 bars and reactor temperature of up to about 200° C. The process employs a liquid medium (e.g. an aromatic such as toluene or an alkane such as hexane, propane or isobutane) in which the polymerization takes place. This results in a suspension of solid polymer particles in the medium. Loop reactors are widely used in slurry processes. Detailed descriptions of slurry polymerization processes are widely reported in the open and patent literature.

In general, a fluidized bed gas phase polymerization reactor employs a "bed" of polymer and catalyst which is fluidized by a flow of monomer which is at least partially gaseous. Heat is generated by the enthalpy of polymerization of the monomer flowing through the bed. Unreacted monomer exits the fluidized bed and is contacted with a cooling system to remove this heat. The cooled monomer is then re-circulated through the polymerization zone together with "make-up" monomer to replace that which was polymerized on the previous pass. As will be appreciated by those skilled in the art, the "fluidized" nature of the polymerization bed helps to evenly distribute/mix the heat of reaction and thereby minimize the formation of localized temperature gradients (or "hot spots"). Nonetheless, it is essential that the heat of reaction be properly removed so as to avoid softening or melting of the polymer (and the resultant-and highly undesirable—"reactor chunks"). The obvious way to maintain good mixing and cooling is to have a very high monomer flow through the bed. However, extremely high monomer flow causes undesirable polymer entrainment.

An alternative (and preferable) approach to high monomer flow is the use of an inert condensable fluid which will boil in the fluidized bed (when exposed to the enthalpy of polymerization), then exit the fluidized bed as a gas, then come into contact with a cooling element which condenses the inert fluid. The condensed, cooled fluid is then returned to the polymerization zone and the boiling/condensing cycle is repeated.

The above-described use of a condensable fluid additive in a gas phase polymerization is often referred to by those skilled in the art as "condensed mode operation" and is described in additional detail in U.S. Pat. Nos. 4,543,399 and 5,352,749. As noted in the '399 reference, it is permissible to use alkanes such as butane, pentanes or hexanes as the condensable fluid and the amount of such condensed fluid preferably does not exceed about 20 weight per cent of the gas phase.

Other reaction conditions for the polymerization of ethylene which are reported in the '399 reference are:

Preferred Polymerization Temperatures: about 75° C. to about 115° C. (with the lower temperatures being preferred for lower melting copolymers—especially those having densities of less than 0.915 g/cc—and the higher temperatures being preferred for higher density copolymers and homopolymers); and Pressure: up to about 1000 psi (with a preferred range of from about 100 to 350 psi for olefin polymerization).

The '399 reference teaches that the fluidized bed process is well adapted for the preparation of polyethylene but further notes that other monomers may be employed—as is the case in the process of this invention.

EXAMPLES

The invention will now be illustrated in further detail by way of the following non-limiting examples. For clarity, the Examples have been divided into three parts, namely Part A (Catalyst Component Synthesis), Part B (Solution Polymerization) and Part C (Gas Phase Polymerization).
Polymer Analysis Gel permeation chromatography ("GPC") analysis was carried out using a commercially available chromatograph (sold under the name Waters 150 GPC) using 1,2,4-trichlorobenzene as the mobile phase at 140° C. The samples were prepared by dissolving the polymer in the mobile phase solvent in an external oven at 0.1% (weight/volume) and were run without filtration. Molecular weights are expressed as polyethylene equivalents with a relative standard deviation of 2.9% and 5.0% for the number average molecular weight (Mn) and weight average molecular weight (Mw), respectively. Melt index (Ml) measurements were conducted according to ASTM method D-1238-82.

Polymer densities were measured using pressed plaques (ASTM method D-1928-90), with a densitometer.

The following abbreviations are used in the Examples:

$^tBu$=tertiary butyl (e.g. $^tBu_3$=tri-tertiary butyl)

Me=methyl

Et=ethyl $^1H$ NMR=proton nuclear magnetic resonance hu iPr=isopropyl

Ph=phenyl

Mw=weight average molecular weight

Mn=number average molecular weight

PD=polydispersity (or Mw/Mn)

PE=polyethylene

Cat=catalyst

Hr=hour

M=molar

MAO=methyl alumoxane

PART A Catalyst Component Synthesis
PART A1 (Prior Art)

Synthesis 1 of Cyclopentadienyltitanium(IV)(tri-t-butylphosphinimine)dichloride

Cyclopentadienyltitanium trichloride (4.025 g, 18.3 mmol) and N-trimethylsilyl-tri-tert-butylphosphinimine (5.47 g, 18.34 mmol) were combined as solids and dry toluene was added. The reaction was heated to 100° C. for 1 hour and then allowed to cool to room temperature. The volatiles were removed in vacuo and the resulting yellow solid was isolated. Yield=7.4 g. 1H NMR ($d_8$-toluene, δ (298K)): 6.39 (singlet, 5H), 1.16 (doublet, J=13.6 Hz, 27H).

Synthesis 2 of Cyclopentadienyltitanium(IV)(tri-t-butylphosphinimine)dichloride

To a solution of $^tBu_3P$=N-H (0.200 g, 0.921 mmol) in dry toluene at room temperature was added a hexane solution of n-BuLi (0.57 mL, 1.6 M, 0.92 mmol). The addition was dropwise and resulted in a slightly turbid solution after 15 minutes of stirring. The lithium salt of the phosphinimine was then added dropwise to a slurry of cyclopentadienyltitanium(IV)trichloride (0.202 g, 0.921 mmol) in toluene. After 4 hours the reaction mixture was filtered through a sintered glass frit and the solvent removed in vacuo to leave the product as a bright green solid. The solid was found to be~98% pure. Yield=247 mg, 67.1%.

Synthesis 3 of Cyclopentadienyltitanium(IV)(tri-t-butylphosphinimine)dichloride $^tBu_3P$=N-H (0.200 g, 0.921 mmol) and cyclopentadienyltitanium(IV)trichloride (0.202, 0.921 mmol) were combined as solids and toluene was added. The reaction was allowed to stir for 30 minutes and then triethylamine (1.30 mL, 9.21 mmol, 10 equiv.) was added dropwise. During the addition, the solution changed from orange to yellow as the sparingly soluble titanium reagent dissolved. The reaction was stirred for an additional 30 minutes and then filtered to remove the precipitated ammonium salt. Removal of the solvent in vacuo gave the product as a yellow crystalline solid. Yield=336 mg, 91.3%.

Synthesis 4 of Cyclopentadienyltitanium(IV)(tri-t-butylphosphinimine)dichloride

To a solution of $^tBu_3P$=N-H (0.347 g, 1.60 mmol) in toluene was added a hexane solution of n-BuLi (1.0 mL, 1.6 M, 1.6 mmol). The addition was dropwise and resulted in a slightly turbid solution after 15 minutes of stirring. The resulting lithium salt of the phosphinimine was then added dropwise to a stirred slurry of titanocene(IV)dichloride (0.398 g, 1.60 mmol) in toluene. After stirring at room temperature for 48 hours the solvent was removed in vacuo. The resulting brown solid was redissolved in the minimum amount of hot toluene and the solution filtered. Heptane was added to the solution and on standing overnight brown crystals of the product grew. These were isolated by decanting off the mother liquor and washing with heptane. Yield=135 mg, 21% (purity=98%).

Synthesis 5 of Cyclopentadienyltitanium(IV)(tri-t-butylphosphinimine[ ]dichloride To a solution of $^tBu_3P$=N-TiCl$_3$ (0.370 g, 1.00 mmol) in toluene was added cyclopentadiene (0.660 g, 1.32 mL, 10.0 mmol). Triethylamine (1.10 g, 1.39 mL, 10.0 mmol) was then added and the solution stirred for 18 hours. At this point the reaction mixture was heated at 80° C. for 2 hours. The toluene was removed under reduced pressure to leave a yellow solid. This was washed with heptane and the product isolated. 1H NMR showed the product contained some starting materials.

Synthesis 6 of Cyclopentadienyltitanium(IV)(tri-t-butylphosphinimine)dichloride $^tBu_3P=N-TiCl_3$ (1.00 g, 2.70 mmol) and CpLi (0.194 g, 2.70 mmol) were combined as solids and toluene was added. The reaction mixture was stirred overnight, filtered through a sintered glass frit and then concentrated in vacuo. The resulting yellow solid was analyzed by NMR and found to be pure product. Yield=971 mg, 81%.

Preparation of Cyclopentadienyltitanium(IV)(tri-tert-butylphosphinimine)(2-N,N-dimethylamino)benzyl Chloride, $C_5H_5Ti(NP^tBu_3)(CH_2C_6H_4N(CH_3)_2)Cl$ To a solution of cyclopentadienyltitanium(IV)(tri-t-butylphosphinimine) dichloride (1.904 g, 4.76 mmol) in anhydrous tetrahydrofuran (THF, 50 mL) at −78° C. was added a solution of 2-N,N-dimethylaminobenzyl lithium (671 mg, 4.76 mmol) in THF (30 mL). A red color started to form immediately and the reaction was allowed to warm to room temperature. The solvent was removed in vacuo and the residue taken up in toluene and filtered. The toluene was then removed and the residues redissolved in hexane at 60° C. The solution was filtered and then placed in a −15° C. freezer. The product formed as a pure orange crystalline solid on standing overnight and was isolated by filtration and pumping to dryness in vacuo. Yield=1.45 g, 61%. 1H NMR ($d_8$-toluene, δ (298K)): 6.9–7.41 (m, Ph-h), 6.11 (s, Cp-M, 3.35 (d, J=9.5 Hz, CHH), 3.03 (d, J=9.5 Hz, CHH), 2.64 (s, N-$CH_3$), 1.22 (d, J=13.2 Hz, $^tBuH$).

PART A2

A2.1 Preparation of Cyclopentadienyltitanium(IV)(tri-tert-butylphosphinimine)(2-N,N-dimethylamino)benzyl Chloride, $C_5H_5Ti(NP^tBu_3)(CH_2C_6H_4N(CH_3)_2)Cl$ To a solution of cyclopentadienyltitanium(IV)(tri-t-butylphosphinimine) dichloride (1.904 g, 4.76 mmol) in anhydrous tetrahydrofuran (THF, 50 mL) at −78° C. was added a solution of 2-N,N-dimethylaminobenzyl lithium (671 mg, 4.76 mmol) in THF (30 mL). A red color started to form immediately and the reaction was allowed to warm to room temperature. The solvent was removed in vacuo and the residue taken up in toluene and filtered. The toluene was then removed and the residues redissolved in hexane at 60° C. The solution was filtered and then placed in a −15° C. freezer. The product formed as a pure orange crystalline solid on standing overnight and was isolated by filtration and pumping to dryness in vacuo. Yield=1.45 g, 61%. 1H NMR ($d_8$-toluene, δ (298K)): 6.9–7.41 (m, Ph-H), 6.11 (s, Cp-h), 3.35 (d, J=9.5 Hz, CHH), 3.03 (d, J=9.5 Hz, CHH), 2.64 (s, N-$CH_3$), 1.22 (d, J=13.2 Hz, $^tBuH$).

A2.2 Preparation of Cyclopentadienyltitanium(III)(tri-tert-butylphosphinimine)(2-N,N-dimethylamino)benzyl, $C_5H_5Ti(NP^tBu_3)(CH_2C_6H_4N(CH_3)_2)$ To a flask containing cyclopentadienyltitanium(IV)(tri-tert-butylphosphinimine)(2-N,N-dimethylamino)benzyl chloride (600 mg, 1.23 mmol) and magnesium powder (1 g, 41 mmol) was added THF (30 mmol). The reaction was stirred for 5 days and then the THF was removed in vacuo. Hexane was added and the reaction flask warmed to 55° C. The solution was then filtered, concentrated in vacuo and cooled to −15° C. The product formed as a purple-red crystalline solid and was isolated by filtration and pumping to dryness in vacuo. Yield=230 mg. Electron Paramagnetic Resonance (ESR) g=1.9752. This g value confirms the presence of the Ti(III) species.

A2.3 Preparation of Cyclopentadienyltitanium(tri-tert-butylphosphinimine)(butadiene), $C_5H_5Ti(NP^tBu_3)(C_4H_6)$ Dry toluene (10 mL) was added to a flask containing cyclopentadienyltitanium(tri-tert-butylphosphinimine) dichloride (844 mg, 2.11 mmol) and magnesium butadiene complex, $Mg(C_4H_6)$, (500 mg, 2.25 mmol) at room temperature. The reaction mixture immediately became dark red and a slight exotherm was observed. After stirring for 1 hour the toluene was removed in vacuo and the product extracted with hexane. The solution was filtered and the hexane removed to leave the desired product as a pure dark red crystalline solid. Yield=663 mg, 82%. 1H NMR ($d_8$-toluene, δ (298K)): 5.66 (s, Cp-H, 4.75 (broad, butadiene), 1.09 (d, J=12.5 Hz).

A2.4 Preparation of Cyclopentadienyltitanium(IV)(tri-tert-butylphosphinimine)-N,N'-dimethylethylenediamine, $C_5H_5Ti(NP^tBu_3)(N(Me)CH_2CH_2N(Me))$ To a solution of N,N'-dimethylethylenediamine (2.24 g, 2.70 mL, 25.4 mmol) in hexanes (15 mL) was slowly added a solution of butyllithium (31.8 mL, 1.6 M in hexanes, 50.7 mmol). A white precipitate of the dilithio salt formed and this was isolated by filtration and dried in vacuo.

A sample of the di-lithium salt of N,N'-dimethylethylenediamine (0.100 g, 1.00 mmol) and cyclopentadienyltitanium(IV)(tri-t-butylphosphinimine) dichloride (0.400 mg, 1.00 mmol) were combined as solids and toluene (15 mL) was added. Upon addition of the solvent the reaction mixture rapidly changed from yellow to a brown, opaque solution. The reaction mixture was stirred for 1.5 hours and then filtered. The solvent was removed in vacuo yielding the product as a purple/brown solid. Yield= 317 mg, 76%. 1H NMR ($d_8$-toluene, δ (298K)): 6.26 (s, Cp-H), 3.4–3.8 (broad multiplet, methylene protons), 2.91 (s, Me), 1.27(d, J=12.4 Hz).

PART B Solution Polymerization

PART B1 Solution Semi-Batch Reactor (SBR) Results

All the polymerization experiments described below were conducted using a solution semi-batch reactor. All the chemicals (solvent, catalyst and cocatalyst) were fed into the reactor batchwise except ethylene which was fed on demand and no removal of product during the polymerization reaction. All the feed streams were purified prior to the reactor by contact with various absorption media to remove catalysts killing impurities such as water, oxygen, sulfur and polar materials as are known to those skilled in the art. All components were stored and manipulated under an atmosphere of purified argon or nitrogen. The SBR uses a programmable logical control (PLC) system with Wonderware 5.1 software for process control. Ethylene polymerizations were performed in a 500 mL Autoclave Engineers Zipperclave reactor equipped with an air driven stirrer and an automatic temperature control system.

Two catalysts were used, namely $C_5H_5Ti(NP^tBu_3)(CH_2C_6H_4N(CH_3)_2)$ (referred to as "RS-676-89" in the following table; synthesis described in Part A, Section A2.2) and the comparative catalyst cyclopentadienyl titanium (IV) tri-t-butylphosphinimine dichloride ("JS304"; synthesis described in Part A, Section A1), were prepared as described in Part A. The catalysts were dissolved in toluene and the catalyst concentrations were between 0.7–5 mg/mL. A commercially available methylalumoxane (PMAO-IP, purchased from Akzo-Nobel) was used in the experiments.

The experiments were carried out as follows:

| | |
|---|---|
| Cyclohexane | 216 mL |
| Catalyst Concentration | 200 μmol/L |
| Cocatalyst | PMAO-IP; Al/Ti = 300 mol/mol |
| Reaction Temperature | 160° C. |
| Reactor Pressure | 140 psig total |
| Stirring Speed | 2000 rpm |

The polymerization time was 10 minutes in each experiment. The reaction was terminated by adding 5 mL of methanol to the reactor and the polymer was recovered by evaporation of the cyclohexane. The polymerization activities were calculated based on the ethylene consumed during the reaction, not the weight of the polymer produced.

Polymer molecular weights and molecular weight distributions were measured by GPC (Waters 150-C) at 140° C. in 1,2,4-trichlorobenzene calibrated using polyethylene standards.

TABLE B1

| | | Polymerization Activity[1] |
|---|---|---|
| Example | Catalyst | Polymerization Activity g PE/mMolcat*hr[1] |
| 1 | RS-676-89 | 2985.0 |
| 2-C | JS304 | 1292.7 |

[1]The calculation of polymerization activity is based on the ethylene uptake.
C: comparative

TABLE B2

| | | Polymer Properties | |
|---|---|---|---|
| Example | Catalyst | Mw(*10$^{-3}$) | Mw/Mn |
| 1 | RS-676-89 | 76.8 | 5.4 |
| 2-C | JS304 | 121 | 2.3 |

C: comparative

The polyethylene produced by the inventive catalyst RS-676-89 has a low molecular weight tail, which contributes to a higher polydispersity of 5.4. The inventive experiment using RS-676-89 showed a different kinetic profile which may be a result of the Ti(III) species. The "initial" activity of the inventive experiment was slower/lower, but the overall activity was high. This is very desirable for commercial-scale polymerizations having a residence time of more than 2 minutes.

PART B2 The Continuous Solution Polymerization

All the polymerization experiments described below were conducted on a continuous solution polymerization reactor. The process is continuous in all feed streams (solvent, monomers and catalyst) and in the removal of product. All feed streams were purified prior to the reactor by contact with various absorption media to remove catalyst killing impurities such as water, oxygen and polar materials as is known to those skilled in the art. All components were stored and manipulated under an atmosphere of purified nitrogen.

All the examples below were conducted in a reactor of 71.5 cc internal volume. In each experiment the volumetric feed to the reactor was kept constant and as a consequence so was the reactor residence time.

The catalyst solutions were pumped to the reactor independently and in some cases were mixed before entering the polymerization reactor (as indicated in the Examples). Because of the low solubility of the catalysts, activators and MAO in cyclohexane, solutions were prepared in purified xylene. The catalyst was activated in-situ (in the polymerization reactor) at the reaction temperature in the presence of the monomers. The polymerizations were carried out in cyclohexane at a pressure of 1500 psi. Ethylene was supplied to the reactor by a calibrated thermal mass flow meter and was dissolved in the reaction solvent prior to the polymerization reactor. If comonomer (for example 1-octene) was used it was also premixed with the ethylene before entering the polymerization reactor. Under these conditions the ethylene conversion is a dependent variable controlled by the catalyst concentration, reaction temperature and catalyst activity, etc.

The internal reactor temperature is monitored by a thermocouple in the polymerization medium and can be controlled at the required set point to +/−0.5° C. Downstream of the reactor the pressure was reduced from the reaction pressure (1500 psi) to atmospheric. The solid polymer was then recovered as a slurry in the condensed solvent and was dried by evaporation before analysis.

The ethylene conversion was determined by a dedicated on line gas chromatograph by reference to propane which was used as an internal standard. The average polymerization rate constant was calculated based on the reactor hold-up time, the catalyst concentration in the reactor and the ethylene conversion and is expressed in l/(mmol*min).

Average polymerization rate $(kp)=(Q/(100-Q))\times(1/[TM])\times(1/HUT)$ where:

Q is the percent ethylene conversion.

[TM] is the catalyst concentration in the reactor expressed in mM.

HUT is the reactor hold-up time in minutes.
Polymer Analysis

Melt index (MI) measurements were conducted according to ASTM method D-1238-82.

Polymer densities were measured on pressed plaques (ASTM D-1928-90) with a densitometer.

Example 1

CpTiNP($^t$Bu)$_3$(butadiene) (from Part A; Section A2.3) was added to the reactor at 9.3×10$^{-6}$ mol/l along with Ph$_3$C B(C$_6$F$_5$)$_4$ (purchased from "Asahi Glass") at B/Ti=1.00 (mol/mol). Both components were mixed in the polymerization reactor. The reaction temperature was 160° C. and 2.1 gram/min of ethylene was continuously added to the reactor. An ethylene conversion of 98.8% was observed (see Table B2.1).

Example 2

CpTiNP($^t$Bu)$_3$(butadiene) was added to the reactor at 9.3×10$^{-6}$ mol/l along with B(C$_6$F$_5$)$_3$ (purchased from "Boulder Scientific") at B/Ti=2.5 (mol/mol). Both components were mixed before the polymerization reactor. The reaction temperature was 160° C. and 2.1 gram/min of ethylene was continuously added to the reactor. An ethylene conversion of 70.7% was observed (see Table B2.1).

Example 3

CpTiNP($^t$Bu)$_3$(butadiene) was added to the reactor at 2.3×10$^{-6}$ mol/l along with Ph$_3$C B(C$_6$F$_5$)$_4$ (Asahi Glass) at B/Ti=1.00 (mol/mol). Both components were mixed in the polymerization reactor. The reaction temperature was 160° C. and 2.1 gram/min of ethylene was continuously added to the reactor. An ethylene conversion of 96.3% was observed (see Table B2.1).

Example 4

CpTiNP($^t$Bu)$_3$(butadiene) was added to the reactor at 5.3×10$^{-6}$ mol/l along with MMAO-7 (purchased from "Akzo-Nobel") at Al/Ti=40.0 (mol/mol). Both components were mixed in the polymerization reactor. The reaction temperature was 160° C. and 2.1 gram/min of ethylene was continuously added to the reactor. An ethylene conversion of 89.4% was observed (see Table B2.1).

Example 5

CpTiNP($^t$Bu)$_3$(butadiene) was added to the reactor at 5.8×10$^{-6}$ mol/l along with MMAO-7 (Akzo-Nobel) at Al/Ti=40.0 (mol/mol). Both components were mixed in the polymerization reactor. The reaction temperature was 160° C. and 2.1 gram/min of ethylene was continuously added to the reactor as was 1.0 ml/min of 1-octene. An ethylene conversion of 89.4% was observed (see Table B2.1).

Example 6

CpTiNP($^t$Bu)$_3$(butadiene) was added to the reactor at 8.1×10$^{-6}$ mol/l along with MMAO-7 (Akzo-Nobel) at Al/Ti=40.0 (mol/mol). Both components were mixed in the polymerization reactor. The reaction temperature was 160° C. and 2.1 gram/min of ethylene was continuously added to the reactor as was 3.0 ml/min of 1-octene. An ethylene conversion of 90.2% was observed (see Table B2.1).

Example 7

CpTiNP($^t$Bu)$_3$(butadiene) was added to the reactor at 8.1×10$^{-6}$ mol/l along with MMAO-7 (Akzo-Nobel) at Al/Ti=40.0 (mol/mol). Both components were mixed in the polymerization reactor. The reaction temperature was 160° C. and 2.1 gram/min of ethylene was continuously added to the reactor as was 5.0 ml/min of 1-octene. An ethylene conversion of 90.4% was observed (see Table B2.1).

Example 8

CpTiNP($^t$Bu)$_3$(butadiene) was added to the reactor at 1.9×10$^{-6}$ mol/l along with MMAO-7 (Akzo-Nobel) at Al/Ti=40.0 (mol/mol) and Ph$_3$C B(C$_6$F$_5$)$_4$ (Asahi Glass) at B/Ti=1.00 (mol/mol). CpTiNP($^t$Bu)$_3$(butadiene) and Ph$_3$C B(C$_6$F$_5$)$_4$ were mixed before the reactor and were subsequently mixed with the MMAO-7 in the reactor. The reaction temperature was 160° C. and 2.1 gram/min of ethylene was continuously added to the reactor as was 3.0 ml/min of 1-octene. An ethylene conversion of 91.3% was observed (see Table B2.1).

Example 9

CpTiNP($^t$Bu)$_3$(butadiene) was added to the reactor at 1.9×10$^{-6}$ mol/l along with MMAO-7 (Akzo-Nobel) at Al/Ti=40.0 (mol/mol) and Ph$_3$C B(C$_6$F$_5$)$_4$ (Asahi Glass) at B/Ti=1.00 (mol/mol). CpTiNP($^t$Bu)$_3$(butadiene) and Ph$_3$C B(C$_6$F$_5$)$_4$ were mixed before the reactor and were subsequently mixed with the MMAO-7 in the reactor. The reaction temperature was 160° C. and 2.1 gram/min of ethylene was continuously added to the reactor as was 5.0 ml/min of 1-octene. An ethylene conversion of 90.5% was observed (see Table B2.1).

Example 10

CpTiNP($^t$Bu)$_3$(butadiene) was added to the reactor at 1.9×10$^{-6}$ mol/l along with MMAO-7 (Akzo-Nobel) at Al/Ti=40.0 (mol/mol) and Ph$_3$C B(C$_6$F$_5$)$_4$ (Asahi Glass) at B/Ti=1.00 (mol/mol). CpTiNP($^t$Bu)$_3$(butadiene) and Ph$_3$C B(C$_6$F$_5$)$_4$ were mixed before the reactor and were subsequently mixed with the MMAO-7 in the reactor. The reaction temperature was 160° C. and 2.1 gram/min of ethylene was continuously added to the reactor as was 1.0 ml/min of 1-octene. An ethylene conversion of 91.3% was observed (see Table B2.1).

Example 11

CpTiNP($^t$Bu)$_3$(butadiene) was added to the reactor at 1.9×10$^{-6}$ mol/l along with MMAO-7 (Akzo-Nobel) at Al/Ti=40.0 (mol/mol) and Ph$_3$C B(C$_6$F$_5$)$_4$ (Asahi Glass) at B/Ti=1.00 (mol/mol). CpTiNP($^t$Bu)$_3$(butadiene) and Ph$_3$C B(C$_6$F$_5$)$_4$ were mixed before the reactor and were subsequently mixed with the MMAO-7 in the reactor. The reaction temperature was 160° C. and 2.1 gram/min of ethylene was continuously added to the reactor. An ethylene conversion of 90.7% was observed (see Table B2.1).

Example 12

CpTiNP($^t$Bu)$_3$(CH$_2$C$_6$H$_4$-2-NMe$_2$) (from Part A; Section A2.2) was added to the reactor at 9.3×10$^{-6}$ mol/l along with Ph$_3$C B(C$_6$F$_5$)$_4$ (Asahi Glass) at B/Ti=1.00 (mol/mol). Both components were mixed in the polymerization reactor. The reaction temperature was 160° C. and 2.1 gram/min of ethylene was continuously added to the reactor. An ethylene conversion of 93.5% was observed (see Table B2.1).

Example 13

CpTiNP($^t$Bu)$_3$(CH$_2$C$_6$H$_4$-2-NMe$_2$) was added to the reactor at 4.6×10$^{-6}$ mol/l along with HNMe$_2$Ph B(C$_6$F$_5$)$_4$ (Akzo-Nobel) at B/Ti=1.00 (mol/mol). Both components were mixed in the polymerization reactor. The reaction temperature was 160° C. and 2.1 gram/min of ethylene was continuously added to the reactor. An ethylene conversion of 91.5% was observed (see Table B2.1).

Example 4

CpTiNP($^t$Bu)$_3$(CH$_2$C$_6$H$_4$-2-NMe$_2$) was added to the reactor at 13.0×10$^{-6}$ mol/l along with MMAO-7 (Akzo-Nobel) at Al/Ti=50.0 (mol/mol). Both components were mixed in the polymerization reactor. The reaction temperature was 160° C. and 2.1 gram/min of ethylene was continuously added to the reactor as was 3.0 ml/min of 1-octene. An ethylene conversion of 89.1% was observed (see Table B2.1).

Example 15

CpTiNP($^t$Bu)$_3$(CH$_2$C$_6$H$_4$-2-NMe$_2$) was added to the reactor at 9.3×10$^{-6}$ mol/l along with MMAO-7 (Akzo-Nobel) at Al/Ti=40.0 (mol/mol) and Ph$_3$C B(C$_6$F$_5$)$_4$ (Asahi Glass) at B/Ti=1.00 (mol/mol). All components were mixed in the reactor. The reaction temperature was 160° C. and 2.1 gram/min of ethylene was continuously added to the reactor. An ethylene conversion of 92.8% was observed (see Table B2.1).

Example 16

CpTiNP($^t$Bu)$_3$(CH$_2$C$_6$H$_4$-2-NMe$_2$) was added to the reactor at 9.3×10$^{-6}$ mol/l along with MMAO-7 (Akzo-Nobel) at Al/Ti=40.0 (mol/mol) and Ph$_3$C B(C$_6$F$_5$)$_4$ (Asahi Glass) at B/Ti=1.00 (mol/mol). All components were mixed in the reactor. The reaction temperature was 160° C. and 2.1 gram/min of ethylene was continuously added to the reactor as was 3.0 ml/min of 1-octene. An ethylene conversion of 93.6% was observed (see Table B2.1).

Comparative Example 17C (C$_5$Me$_5$)$_2$ZrCl$_2$ (purchased from "Strem") was added to the reactor at 37×10$^{-6}$ mol/l along with MMAO-3 (Akzo- Nobel, Al/Ti=400 mol/mol). The reaction temperature was 140° C. and 1.0 gram/min of ethylene was continuously added to the reactor. An ethylene conversion of 55.5% was observed (see Table B2.1).

Comparative Example 18C $(C_5Me_5)_2ZrCl_2$ (Strem) was added to the reactor at $37 \times 10^{-6}$ mol/l along with MMAO-3 (Akzo-Nobel, Al/Ti= 400 mol/mol). The reaction temperature was 160° C. and 1.0 gram/min of ethylene was continuously added to the reactor. An ethylene conversion of 35.6% was observed (see Table B2.1).

Comparative Example 19C $(C_5Me_5)_2ZrCl_2$ (Strem) was added to the reactor at $37 \times 10^{-6}$ mol/l along with MMAO-3 (Akzo-Nobel, Al/Ti= 400 mol/mol). The reaction temperature was 160° C. and 2.1 gram/min of ethylene was continuously added to the reactor. An ethylene conversion of 37.4% was observed (see Table B2.1).

Comparative Example 20C rac-Et(ind)$_2$ZrCl$_2$ (purchased from "Witco") was added to the reactor at $37 \times 10^{-6}$ mol/l along with MMAO-3 (Akzo-Nobel, Al/Ti=400 mol/mol). The reaction temperature was 160° C. and 2.1 gram/min of ethylene was continuously added to the reactor. An ethylene conversion of 94.6% was observed (see Table B2.1).

Comparative Example 21C rac-Et(ind)$_2$ZrCl$_2$ (Witco) was added to the reactor at $37 \times 10^{-6}$ mol/l along with MMAO-3 (Akzo-Nobel, Al/Ti= 400 mol/mol). The reaction temperature was 160° C. and 2.1 gram/min of ethylene and 3.25 ml/min of 1-octene was continuously added to the reactor. An ethylene conversion of 94.8% was observed (see Table B2.1).

PART C Gas Phase Polymerization
Catalyst Preparation and Polymerization Testing Using a Semi-Batch, Gas Phase Reactor The catalyst preparation methods described below employ typical techniques for the syntheses and handling of air-sensitive materials. Where appropriate, elemental compositions of the supported catalysts were measured by Neutron Activation analysis and a reported accuracy of ±1% (weight basis).

The supported catalysts were prepared by initially supporting MAO on a silica support, followed by deposition of the catalyst component.

All the polymerization experiments described below were conducted using a semi-batch, gas phase polymerization reactor of total internal volume of 2.2 L. Reaction gas mixtures, including ethylene/butene mixtures (96 mole % ethylene, 4 mole % butene) were measured to the reactor on a continuous basis using a calibrated thermal mass flow meter, following passage through purification media as described above. A predetermined mass of the catalyst sample as added to the reactor under the flow of the inlet gas with no pre-contact of the catalyst with any reagent, such as a catalyst activator. The catalyst was activated in-situ (in the polymerization reactor) at the reaction temperature in the presence of the monomers, using a metal alkyl complex which has been previously added to the reactor to remove adventitious impurities. Purified and rigorously anhydrous sodium chloride was used as a catalyst dispersing agent.

The internal reactor temperature is monitored by a thermocouple in the polymerization medium and can be controlled at the required set point to +/−1.0° C. The duration of the polymerization experiment was one hour. Following the completion of the polymerization experiment, the polymer was separated from the sodium chloride and the yield determined.

Table C1 illustrates data concerning the Al/transition metal ratios of the supported catalyst and polymer yield. Polymer properties are shown in Table C2.

TABLE B2.1

| Example | Total Flow to Reactor (ml/min) | Catalyst Concentration (mol × 10$^6$) | Ethylene Conversion (%) | Calculated Polymerization Rate (kp) (l/mmol × min) | Polymer Density (g/cc) | Polymer Melt Index | Mn × 10$^{-3}$ | Mw × 10$^{-3}$ |
|---|---|---|---|---|---|---|---|---|
| 1 | 27.0 | 9.3 | 98.8 | 3475 | | | | |
| 2 | 27.0 | 9.3 | 79.7 | 98 | | | | |
| 3 | 27.0 | 2.3 | 96.3 | 4246 | | | | |
| 4 | 27.0 | 5.3 | 89.4 | 599 | 0.940 | | | |
| 5 | 27.0 | 5.8 | 89.4 | 549 | 0.922 | | | |
| 6 | 27.0 | 8.1 | 90.2 | 431 | 0.909 | | | |
| 7 | 27.0 | 8.1 | 90.4 | 437 | | | | |
| 8 | 27.0 | 1.9 | 91.3 | 2132 | 0.911 | 0.57 | | |
| 9 | 27.0 | 1.9 | 90.5 | 1934 | 0.905 | 1.39 | | |
| 10 | 27.0 | 1.9 | 91.3 | 2140 | 0.920 | 0.71 | | |
| 11 | 27.0 | 1.9 | 90.7 | 1994 | 0.940 | 0.002 | | |
| 12 | 27.0 | 9.3 | 93.5 | 584 | | | | |
| 13 | 27.0 | 4.6 | 91.5 | 883 | | | | |
| 14 | 27.0 | 13.0 | 89.1 | 237 | 0.913 | 0.019 | | |
| 15 | 27.0 | 9.3 | 92.8 | 526 | 0.942 | 0.004 | | |
| 16 | 27.0 | 9.3 | 93.6 | 601 | 0.912 | 2.63 | | |
| 17C | 27.0 | 37.0 | 55.5 | 13 | — | 880 | 2.7 | 10.0 |
| 18C | 27.0 | 37.0 | 35.6 | 6 | — | — | 1.8 | 7.5 |
| 19C | 27.0 | 37.0 | 37.4 | 6 | — | 620 | 3.3 | 12.0 |
| 20C | 27.0 | 37.0 | 94.6 | 179 | — | 1300 | 3.9 | 14.0 |
| 21C | 27.0 | 37.0 | 94.8 | 186 | 0.925 | very high | 2.6 | 10.0 |

TABLE C1

| Complex | mmol Complex | Supp.* | mg of Catalyst | Yield | gPe/g Metal | gPe/g Catalyst | Al/M Ratio |
|---|---|---|---|---|---|---|---|
| CpTi(III)[NP(tBu)$_3$]CH$_2$-o-NMe$_2$C$_6$H$_4$ | 0.1 | 1 g | 37 | 15 | 84672 | 405 | 95 |
| CpTi[NP(tBu)$_3$](butadiene) | 0.1 | 1 g | 52 | 52 | 208885 | 1000 | 86 |
| CpTi[NP(tBu)$_3$][N(Me)EtN(Me)] | 0.1 | 1 g | 43 | 12 | 125570 | 1145 | 96 |

*Support is a supported MAO-on-silica (purchased from Witco)

TABLE C2

| Example | Catalyst | Polymer Properties | |
|---|---|---|---|
| | | Mw (*10$^{-3}$) | Mw/Mn |
| 1 | CpTi(III)[NP(tBu)$_3$]CH$_2$-o-NMe$_2$C$_6$H$_4$ | 169 | 4.6 |
| 2 | CpTi[NP(tBu)$_3$](butadiene) | 285 | 4.4 |
| 3 | CpTi[NP(tBu)$_3$][N(Me)EtN(Me)] | 682 | 4.0 |

[1]From Part A; section A2.2
[2]From Part A; section A2.3
[3]From Part A; section A2.4

What is claimed is:

1. A process for the polymerization of ethylene characterized in that said process is conducted in the presence of:

(a) an organometallic complex defined by the formula:

wherein Cp is a ligand selected from the group consisting of unsubstituted cyclopentadienyl, substituted cyclopentadienyl, unsubstituted indenyl substituted indenyl substituted fluorenyl and unsubstituted fluorenyl; L is one, and only one, activatable ligand; M is a metal selected from Ti and Zr; and Pl is a phosphinimine ligand defined by the formula:

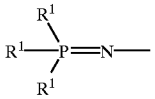

wherein each R is independently selected from the group consisting of a hydrogen atom, a halogen atom, $C_{1-20}$ hydrocarbyl radicals which are unsubstituted by or further substituted by a halogen atom, a $C_{1-8}$ alkoxy radical, an amido radical, a $C_{6-10}$ aryl or aryloxy radical, a silyl radical of the formula:

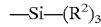

wherein each $R^2$ is independently selected from the group consisting of hydrogen, a $C_{1-8}$ alkyl or alkoxy radical, $C_{6-10}$ aryl or aryloxy radicals, and a germanyl radical of the formula:

wherein $R^2$ is as defined above; and (b) an activator.

2. The process of claim 1 wherein said ethylene is copolymerized with a minor amount of an alpha olefin having from 3 to 10 carbon atoms.

3. The process of claim 1 wherein said activator is an ionic activator.

4. The process of claim 1 wherein each $R^1$ is tertiary butyl and M is titanium (III).

* * * * *